US009636431B2

(12) United States Patent
Teeling et al.

(10) Patent No.: US 9,636,431 B2
(45) Date of Patent: May 2, 2017

(54) DISPENSER, AND REFILL

(75) Inventors: Matthew Teeling, Reading (GB); Paul Wonnacott, Esher (GB)

(73) Assignee: Vectair Systems Limited, Basingstoke (GB)

( * ) Notice: Subject to any disclaimer, the term of this patent is extended or adjusted under 35 U.S.C. 154(b) by 333 days.

(21) Appl. No.: 13/591,965

(22) Filed: Aug. 22, 2012

(65) Prior Publication Data
US 2013/0056552 A1 Mar. 7, 2013

(51) Int. Cl.
| B05B 1/08 | (2006.01) |
| A61L 9/14 | (2006.01) |
| B05B 17/06 | (2006.01) |
| B05B 1/30 | (2006.01) |
| B05B 17/00 | (2006.01) |

(52) U.S. Cl.
CPC ............ *A61L 9/14* (2013.01); *B05B 17/0607* (2013.01); *B05B 17/0676* (2013.01); *A61L 2209/132* (2013.01); *A61L 2209/133* (2013.01); *B05B 1/30* (2013.01); *B05B 17/0646* (2013.01)

(58) Field of Classification Search
CPC .. A61L 9/14; A61L 2209/133; B05B 17/0607
USPC ............................... 239/102.2, 407; 220/694
See application file for complete search history.

(56) References Cited

U.S. PATENT DOCUMENTS

| 5,297,734 A * | 3/1994 | Toda ................... B05B 17/0646 239/102.2 |
| 6,062,425 A * | 5/2000 | Brown ..................... A47K 5/12 222/1 |
| 6,659,364 B1 * | 12/2003 | Humberstone ..... B05B 17/0646 239/102.1 |
| 2008/0314930 A1 * | 12/2008 | Green .................. B67D 3/0035 222/185.1 |
| 2010/0206306 A1 * | 8/2010 | Feriani ................. A61M 11/005 128/203.12 |

(Continued)

FOREIGN PATENT DOCUMENTS

| EP | 1382339 A1 | 1/2004 |
| EP | 2216100 A1 | 8/2010 |

(Continued)

OTHER PUBLICATIONS

EPO Extended Search Report; Application No. 12181952.8-2113; Nov. 29, 2012.

(Continued)

*Primary Examiner* — Arthur O Hall
*Assistant Examiner* — Joel Zhou
(74) *Attorney, Agent, or Firm* — Westman, Champlin & Koehler, P.A.; Z. Peter Sawicki; Amanda M. Prose

(57) ABSTRACT

A dispenser capable of dispensing a fluid via a vertically-oriented piezo device comprises a reservoir containing a fluid to be dispensed, an outlet at a base portion of the reservoir, leading to a dispensing port that comprises a piezo element drivable to vibrate and thereby dispense fluid from the dispensing port, a bleed tube communicating at one end with the dispensing port, extending therefrom to a location above the dispensing port, and including a selectively closeable valve, and a source of below-atmospheric pressure to the portion of the reservoir above the fluid. Embodiments of refills suitable for such a dispensing apparatus are also described.

5 Claims, 5 Drawing Sheets

(56) References Cited

U.S. PATENT DOCUMENTS

2013/0327322 A1* 12/2013 Bentvelsen .......... A61M 11/005
                                                    128/200.16

FOREIGN PATENT DOCUMENTS

| JP | 59222246   | * 12/1984 | ............. B05B 17/06 |
| JP | 59222246 A |   12/1984 |                          |
| JP | 198697066  | *  5/1986 | ............. B05B 17/06 |

OTHER PUBLICATIONS

European Combined Search Examination Report under Sections 17 and 18(3) for for Application No. GB1115123.0.

* cited by examiner

DISPENSER, AND REFILL

FIELD OF THE INVENTION

The present invention relates to a dispenser, and its associated refills. The can be used to dispense any of a variety of materials into an aerosol form, such as (but not limited to) air freshening compositions or other chemicals requiring automatic dosing.

BACKGROUND ART

Dispensers are commonly provided in washrooms and similar facilities, in order to improve their overall environmental condition. In the past, various solid materials were utilized which sublimated, thereby dispersing a substitute odour for the odour found in public facilities. In order to enhance the dispersion of such sublimating materials, many suppliers developed powered fan devices which assisted in the dispersal of the sublimated material. Such devices are well known in the art, and an example is shown in U.S. Pat. No. 4,830,791 entitled "Odor Control Device", which discloses a solid dispensing device.

More recently, odour control devices where a pressurized aerosol container is utilized have become well known in the art. Aerosol-type dispensing devices typically include a battery-powered motor that actuates the nozzle on the aerosol container on a periodic basis. These conventional dispensing devices have significant disadvantages. Aerosol cans require propellant gases, and whilst CFC-free propellants have been identified, these tend to require volatile organic compounds (VOCs), propanol, isobutanes and the like which are coming under increasing scrutiny. Several jurisdictions have introduced legislation aimed at reducing or elimination the unnecessary use of such chemicals.

It would therefore be desirable to deliver the scent directly, i.e. by evaporation or other dispersion of the scent composition itself, avoiding the need for carrier and propellant chemicals. This has been achieved for the home environment by SC Johnson, Inc. with the Glade® Wisp device, which uses a piezo element to disperse a scent formulation into the air by vibrating at high frequency while in contact with a small volume of the formulation. This aerosolises the formulation, dispersing it as required. However, such devices are problematic in that the volume of formulation that is in contact with the piezo must be closely controlled; if too large, the piezo does not resonate and the formulation is not dispensed. This requires the formulation to be delivered to a horizontally-disposed piezo element via a wick.

SUMMARY OF THE INVENTION

As a result of this limitation, the piezo must be mounted in a horizontal disposition. This is acceptable for home use, where the device will be mounted at a low location within the room. Thus, the fragrance is dispensed upwards into the room. However, it is unsuitable for use in corporate or communal washrooms, where the dispenser must be fitted high up to limit vandalism or other tampering. The use of a Wisp-type device in such a location would not result in an effective dispensing of the fragrance into the room, as most of the fragrance would be captured by the ceiling panel above the device.

There still remains, therefore, a need for an effective fragrance dispenser that can be mounted in an elevated location (typically more than 6 feet or 2 meters from the floor) and that can dispense a fragrance without the use of excessive propellant compositions and the like. For corporate and communal use, it would also be preferable for the device to be battery-operated, rather than a plug-in device requiring a mains electrical supply, as there is rarely a mains electrical supply at the required location.

We have succeeded in creating a device which controls the rate of flow of a fragrance formulation onto a vertically-oriented piezo device. This therefore allows a piezo-based dispenser to be used in corporate and communal environments, avoiding all propellant gases and reducing the VOC usage dramatically. Some solvents will be needed in order to set the viscosity of the fragrance at the correct level, but this will be small in comparison with existing aerosol devices.

In its first aspect, the present invention therefore provides a dispensing apparatus, comprising a reservoir containing a fluid to be dispensed, an outlet at a base portion of the reservoir, leading to a dispensing port that comprises a piezo element drivable to vibrate and thereby dispense fluid from the dispensing port, a bleed tube communicating at one end with the dispensing port, extending therefrom to a location above the dispensing port, and including a selectively closeable valve, and a source of below-atmospheric pressure to the portion of the reservoir above the fluid.

The piezo element is preferably porous, thereby to permit dispensing from a front side of the element of fluid contacting the element on a rear side. In this way, the piezo element can be located at the end of a conduit and dispense fluid from the conduit. However, we have found that such piezo elements are sensitive to the pressure of fluid behind them; too high, and the piezo element will be too heavily damped to be able to vibrate in the correct manner. The above-defined arrangement of a bleed tube with selectively closeable valve, and source of below-atmospheric pressure, ensures that an acceptable pressure is maintained in combination with a useful flow rate.

The source of below-atmospheric pressure can be a piston. This can be arranged to withdraw air or otherwise expand the volume above the fluid in the reservoir, thereby creating a zone of reduced air pressure.

Most dispensing apparatus have an openable cover concealing at least part of the apparatus. This provides a neat external appearance for the device and hinders unauthorised tampering. The cover is opened to allow access by service staff who can then replace the refill (etc). Ideally, the piston is operatively connected to the cover so as to impose the below-atmospheric pressure to the reservoir as a result of the action of closing the cover. This ensures that the reduced pressure is consistently applied. Where a piston is used, the plunger of the piston can be acted on by the cover as it closes.

In a similar manner, such a cover can also be operatively connected to the selectively closeable valve so as to close the valve on closing the cover.

We prefer that both the bleed tube and the source of below-atmospheric pressure are provided, for reasons set out herein. However, the present invention also relates to a dispenser as set out above, but with just the bleed tube, and to a dispenser as set out above, but with just the source of below-atmospheric pressure.

In a second aspect, the present invention relates to a refill, suitable for a dispensing apparatus such as that defined above. The refill comprises an internal reservoir containing a fluid to be dispensed and having an outlet at a lower extremity, and an upwardly-extending fluid conduit, separate from the reservoir.

A port can be provided at an upper extremity of the reservoir, for application of a below-atmospheric pressure.

Further, a port can be provided at a lower extremity of the fluid conduit, for connection to the dispensing apparatus. A port can also be provided at an upper extremity of the fluid conduit, for connection to a selectively closeable valve. The refill can thus comprise a total of four ports, two at a lower extremity and two at an upper extremity.

Other designs of refill may be possible, co-operating of course with the design of the dispenser. For example, more or less of the dispenser apparatus may be integrated into the refill; the selectively closeable valve could be included or (alternatively) the fluid conduit could be omitted from the refill and made a permanent part of the dispenser.

Thus, in a third aspect of the invention, we propose a refill for a dispensing apparatus, comprising a reservoir containing a fluid to be dispensed with an outlet at a lower extremity of the reservoir and a port at an upper extremity of the reservoir for application of a below-atmospheric pressure.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
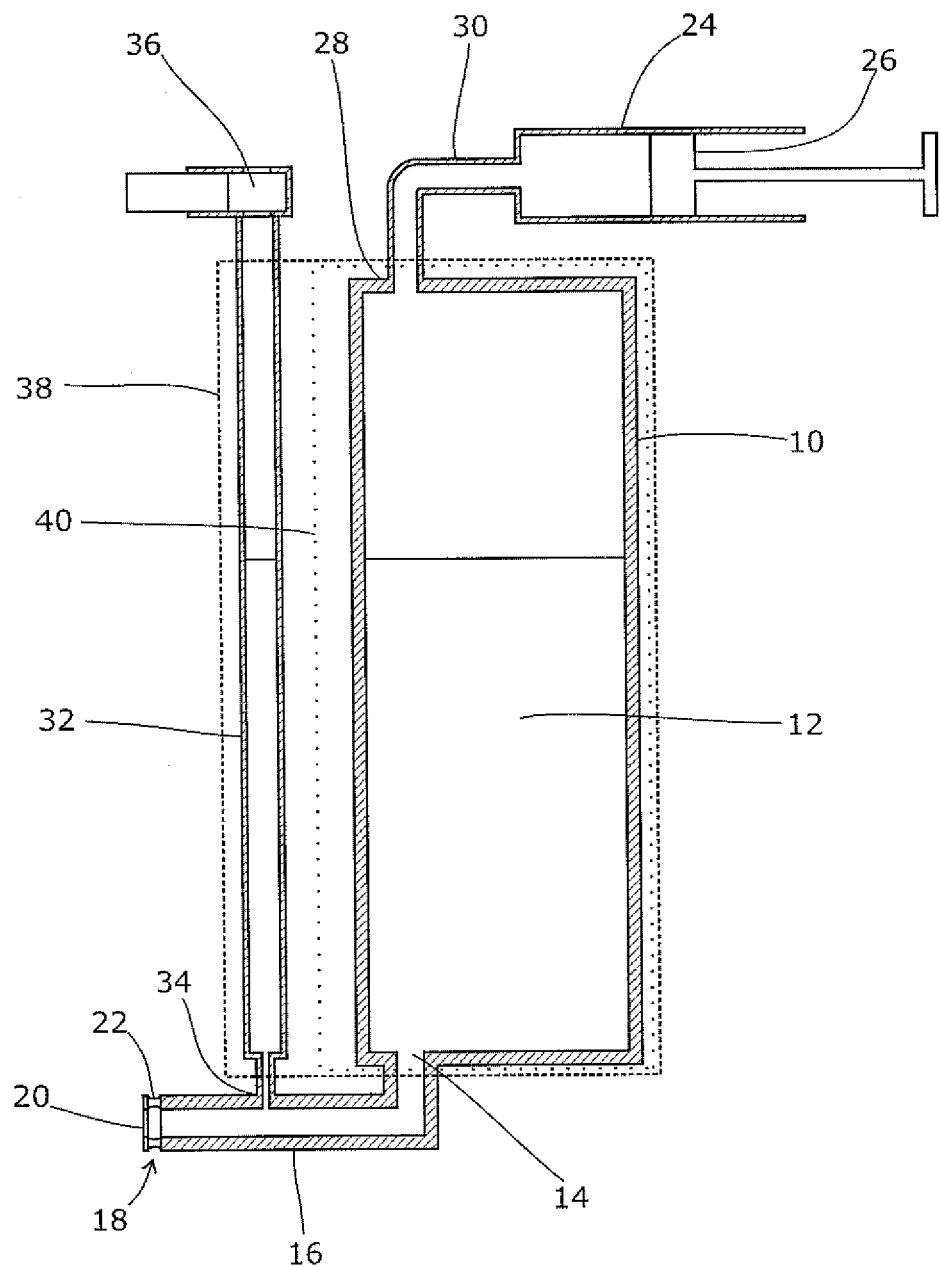
FIG. 1 illustrates the principle of operation of the device.

FIG. 1 illustrates the principle involved in the device. A reservoir 10 contains an amount of fluid 12 which is to be dispensed into the surrounding room. An outlet 14 at the base of the reservoir 10 allows the fluid to flow under gravity out of the reservoir 10 and along a conduit 16 to a dispensing zone 18. This consists of an end to the outlet conduit 16, over which is secured a disc-shaped porous ultrasonic piezo element 20, held in place over the end of the conduit 16 by a flexible seal 22.

When powered by an electrical signal, the piezo element vibrates with a high resonant frequency of about 100-120 kHz. Fluid adsorbed into the rear of the porous disc of the element is then atomised and finely dispersed into the air in front of the element.

We have found, however, that a simple arrangement as described above does not work satisfactorily. Allowing the fluid to flow under gravity to the rear of the piezo element creates too high a pressure behind the element, overloading it and preventing satisfactory resonance. As a result, there is little or no atomisation of the liquid and very little is dispensed.

Two further aspects of the device work together to control the fluid pressure behind the piezo element and ensure that the fluid pressure behind the piezo element is controlled. The first is a source of below-atmospheric pressure that is applied to the volume above the fluid 12 within the reservoir 10. This comprises a syringe 24 in which moves a piston 26, and which is connected to a port 28 at the top of the reservoir 10 via a low pressure conduit 30. As the piston 26 is withdrawn, it will expand any air in the syringe, together with the air in the conduit 30 and any air in the reservoir 10 above the level of the fluid 12. This will create a low pressure zone above the fluid 12 and assist in reducing the pressure behind the piezo element 20.

The second is a bleed tube 32, disposed alongside the reservoir 10. This is generally vertical, and extends from a junction 34 with the outlet conduit 16 just behind the dispensing zone 18, upwards to a point above the dispensing zone 18 and proximate the top of the reservoir 10. A valve 36 at the upper end of the bleed tube 32 is selectively closeable.

The valve 36 is left open during filling or replacement of the reservoir 10. As a result, fluid 12 can flow into the bleed tube 32 via the outlet conduit 16 and the junction 34, expelling air via the valve 36. Before bringing the dispenser into service, the valve 36 is closed (and the piston 26 is withdrawn). The result is that as fluid is dispensed via the piezo element 20, the fluid level in the reservoir 10 will fall. This will seek to draw down the fluid level in the bleed tube, reducing the pressure of the air in the bleed tube above the fluid level. This will assist further in reducing the fluid pressure behind the piezo element 20 and thus control the flow of fluid onto the rear of the piezo element.

Together, these two measures allow sufficient control of the fluid pressure to the rear of the piezo element to allow dispensing of the fluid in the reservoir over a typical service cycle of 30, 60 or 90 days. Whilst both serve to reduce the air pressure above the fluid in the period before and/or during dispensing, and thus either could be used independently, we find that the combination of both has advantages in that neither needs to be particularly aggressive. In other words, the syringe does not need to achieve an exceptionally low pressure; it can thus be primed by the force of (for example) the dispenser door being closed, and does not meet significant leakage problems during a typical service interval. Likewise, the bleed tube does not need to be particularly long, and can thus fit into the approximate size of the reservoir and can be filled by flowback from the reservoir without other assistance.

FIG. 1 shows a dotted outline 38 which encompasses the reservoir 10 and the bleed tube 32. This could form a suitable delineation between the fixed section of the dispenser and a removable refill. Suitable seals could be provided at the top and bottom of the bleed tube, and at the outlet 14 and port 28 of the reservoir, enabling a single removable item to be defined that includes the reservoir and bleed tube. Once the reservoir is exhausted, this item could be removed and replaced with a fresh item (or a recycled and refilled item).

Alternatively, a smaller refill unit 40 could be defined, including only the reservoir 10 and not the bleed tube 32. Thus would have the advantage that the (potentially disposable) refill would cost slightly less, but the larger refill 38 has the advantage that the bleed tube 32 can be placed in front of the reservoir 10, placing the junction 34 proximate the dispensing zone 18 without the bleed tube 32 obstructing removal of the refill.

FIGS. 2 to 6 show a practical implementation of the principle shown in FIG. 1, adopting the larger refill 38. Thus, referring to FIGS. 2, 3 and 4, the dispenser 100 comprises a backplate 102 that can be attached to an upright wall or the like at a suitable elevated location so as to deter tampering (etc). Typically, this is approximately 6 feet (2 meters) from the ground, or higher. The backplate 102 carries a cover 104, shown in an open position, which is hinged to the backplate 102 at its upper edge. Thus, to install or service the dispenser, an operative can lift the cover (after disengaging a suitable latch or lock) to expose the interior of the dispenser.

Figure 2:
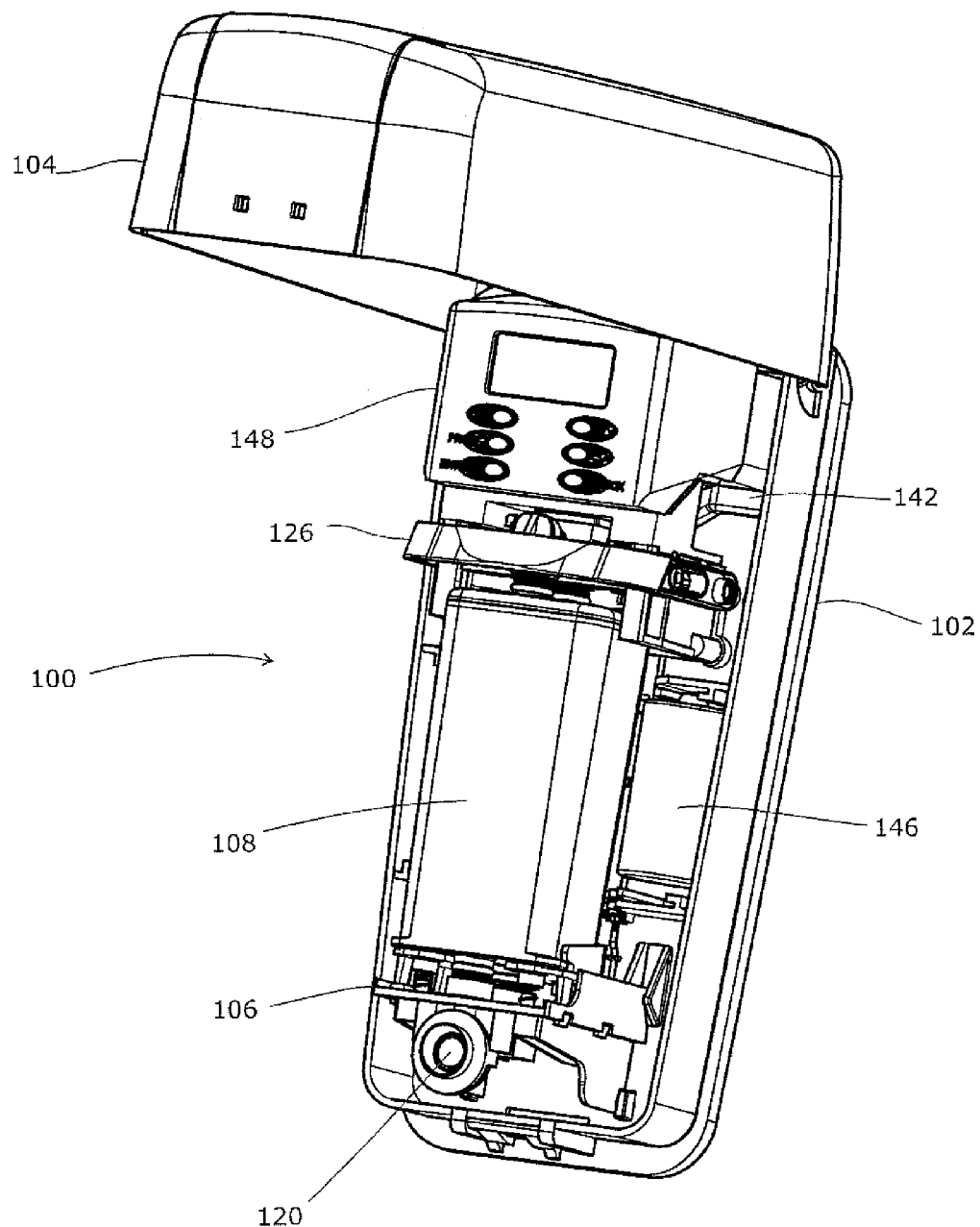
FIG. 2 shows a dispenser being an embodiment of the present invention, with its lid open.
Figure 3:
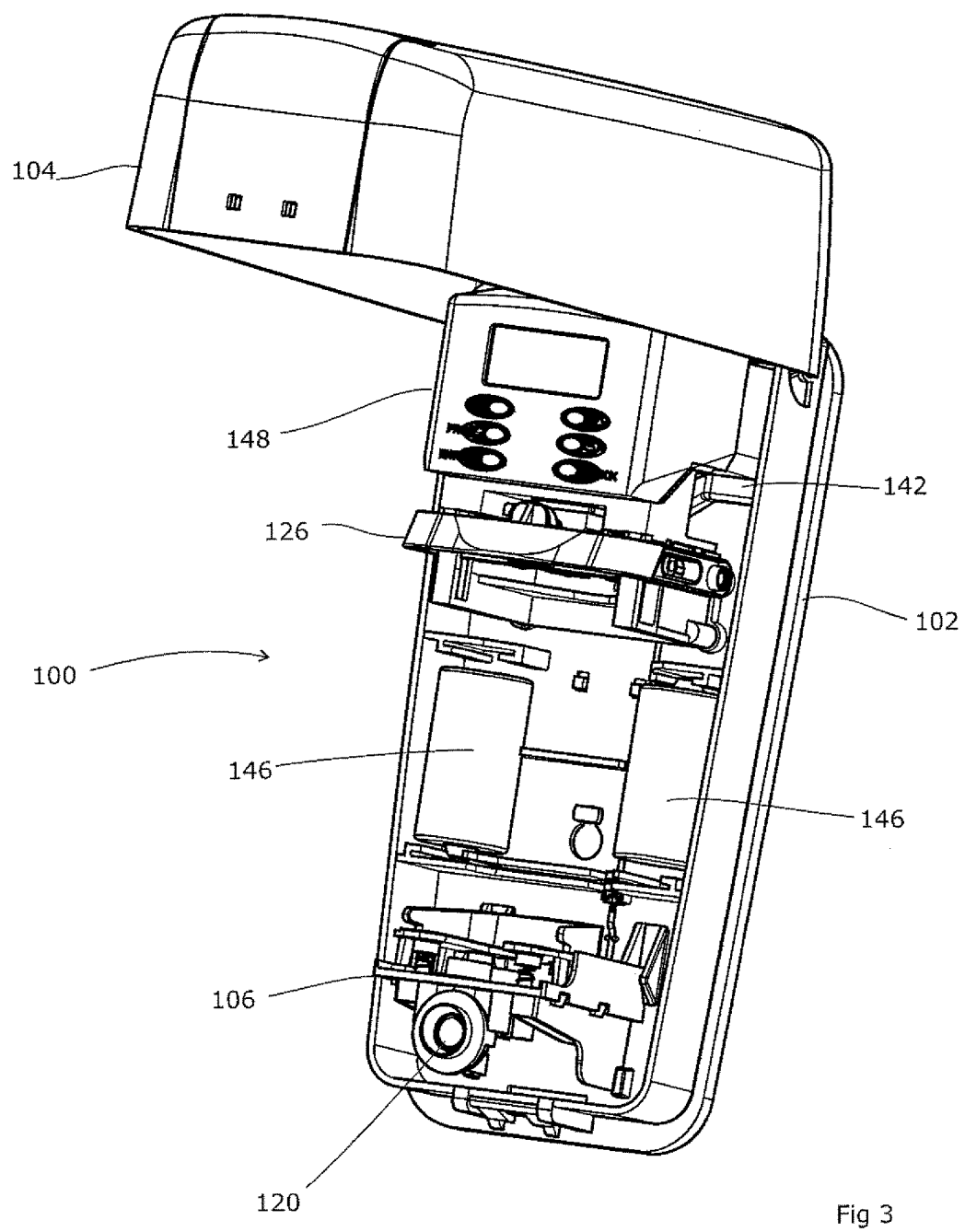
FIG. 3 shows the dispenser of FIG. 2, with the refill cartridge removed.
Figure 4:
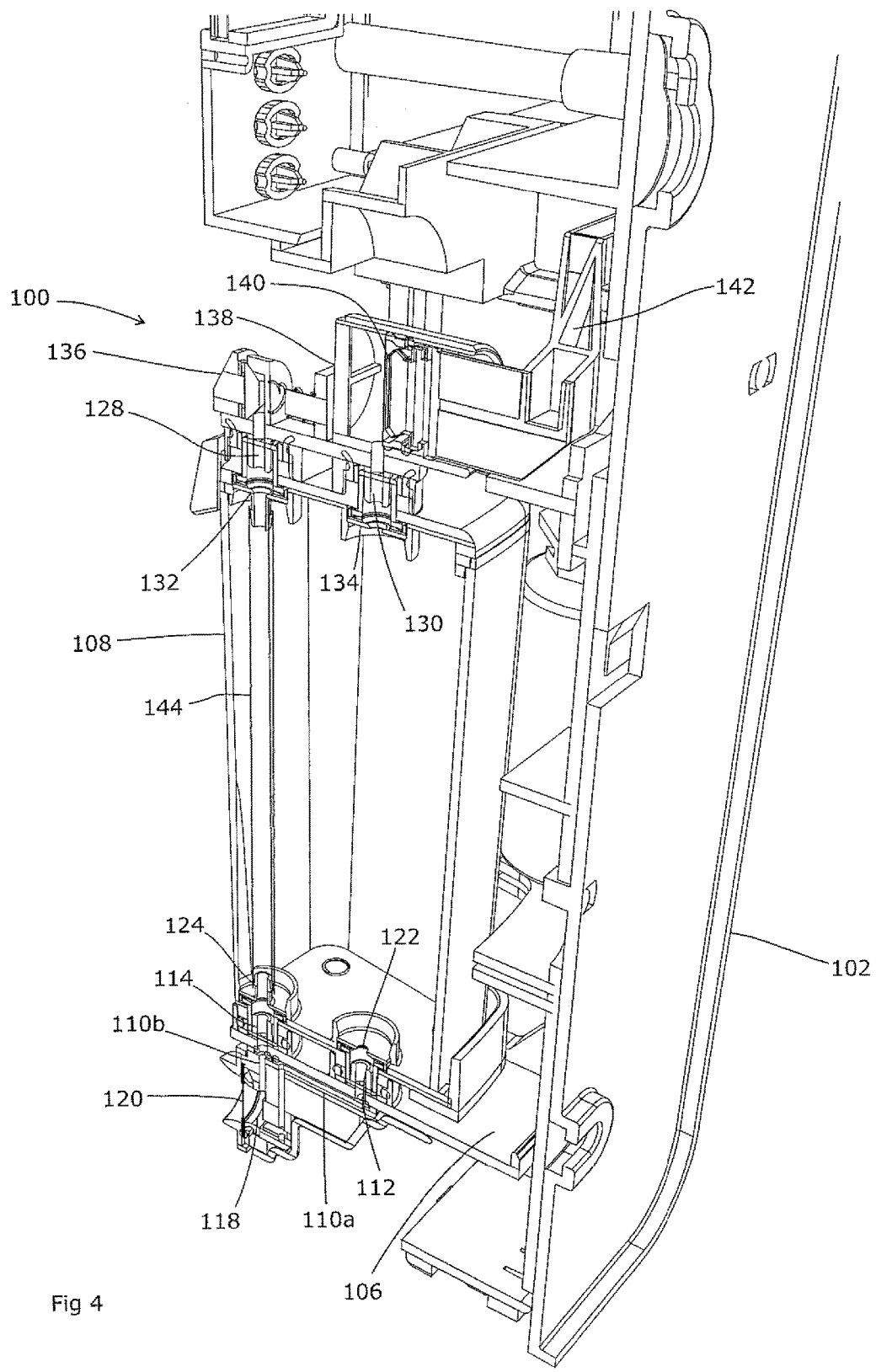
FIG. 4 shows a vertical section through the dispenser of FIG. 2.

Within the dispenser 100, there is a lower shelf 106 onto which a refill unit 108 can be placed. FIGS. 2 and 4 show the refill 108 in place, FIG. 3 shows the dispenser 100 with the refill unit 108 removed. Below the shelf 106 are a pattern of outlet conduits 110*a*, 110*b*; these lead from a pair of lower bayonet fixings 112, 114 (respectively) to a dispensing zone 118 in the form of a cavity closed at its front face by a piezo disc 120. Each of the bayonet fixings 112, 114 engage with a corresponding outlet 122, 124 on the base of the refill unit as will be described. The outlets 122, 124 are closed with septum-type seals to prevent leakage prior to installation.

At the upper end of the dispenser 100, a clamp bar 126 is provided which can be raised or lowered as necessary. In its lowered position it is spaced above the lower shelf 106 so as to retain the refill 108 in a snug grip. In its raised position, it allows the refill to be disengaged from the lower bayonet fixings 112, 114 and removed from the dispenser 100. On the underside of the clamp bar 126, there are a pair of upper bayonet fixings 128, 130 which engage with corresponding ports 132, 134 on the upper face of the refill 108. The upper bayonet fixing 128 leads to a valve 136 which is normally open but pressed into a closed state when the cover 104 is closed. Upper bayonet fixing 130 leads to the interior of a piston chamber 138; a piston 140 is withdrawn in the piston chamber 138 by levers 142 which extend rearwardly from the piston 140 and then outwardly. Thus, as the cover 104 is pressed shut, it presses on the levers 142 urging them towards the backplate 102, against a spring bias (not shown). This draws the piston 140 back within the piston chamber 138.

Within the refill 108, a tube 144 is fitted to the outlet 124 (at one end) and to the port 132 at the other. This acts as the bleed tube, extending from the dispensing zone 118 upwards to the valve 136. The space within the refill 108 around the tube 144 (but not including the interior of the tube 144) acts as the reservoir and is filled with a fluid to be dispensed.

Thus, as described with reference to FIG. 1, the dispenser is prepared for use by opening the cover 104, which opens the valve 136 and allows the piston to move forward (away from the backplate 102) under the force of the spring bias. The clamp bar 126 is lifted and any refill 108 that is present is removed. A fresh refill 108 is obtained, and is placed over the lower bayonet fixings 112, 114. The clamp bar 126 is then lowered, forcing the bayonet fixings into place and allowing fluid to flow from the reservoir within the refill 108 into the dispensing zone 118 and the bleed tube 144. The cover 104 is then closed, closing the valve 136 and withdrawing the piston 140 thereby creating a low pressure zone above the fluid in the reservoir.

Batteries 146 are provided either side of the refill 108 and provide electrical power to a control unit 148 located above the clamp bar 126. This provides power to the piezo element 120 according to a predetermined program which may be (for example) as described in our earlier patent applications GB 2392438, GB 2392439 and GB 2392440. In outline, these provide for periodic activation of the dispenser as required to provide sufficient fragrance to a room over a period of (typically) between 30 and 90 days. In this embodiment, it will send a suitable drive signal to the piezo element 120 as and when a dispensing event is required.

Figure 5:
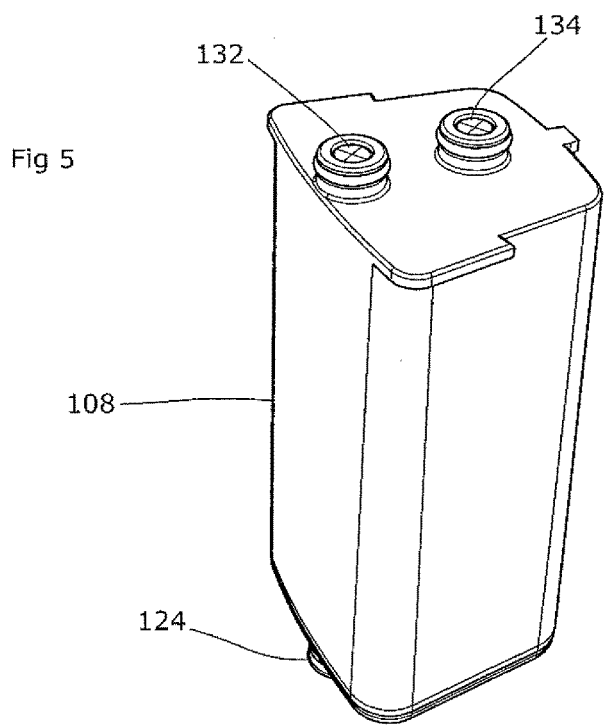
FIG. 5 shows the refill cartridge.
Figure 6:
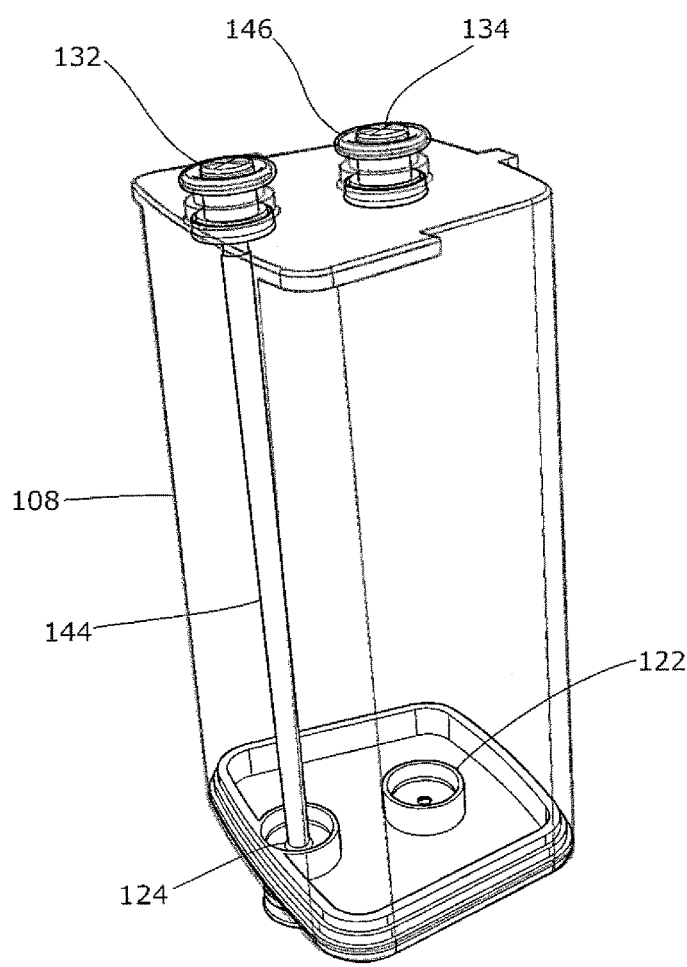
FIG. 6 shows a semi-transparent view of the refill cartridge.

FIGS. 5 and 6 show the refill 108, FIG. 6 in a part-transparent style so as to illustrate the bleed tube 144 in the interior, linking the outlet 124 with the port 132. Outlet 122 allows fluid to be drained from the interior of the refill 108 around the tube 144, and port 134 allows access to the air space above the fluid, permitting the below-atmospheric pressure to be applied. All four outlets and ports are sealed with septum seals which close in the absence of a bayonet fixing thereby preventing leakage, and open when pierced by a bayonet fixing to allow passage of the relevant fluid or gas. Each is also provided with an external O-ring seal 146 to provide additional sealing.

Thus, the present invention provides a dispenser able to dispense a low-VOX fluid that is not aerosol-based, from an elevated location.

It will of course be understood that many variations may be made to the above-described embodiment without departing from the scope of the present invention.

The invention claimed is:

1. A dispensing apparatus, comprising;

a reservoir containing a fluid to be dispensed in an aerosol form;

an outlet at a base portion of the reservoir, leading along a conduit to a dispensing port at an end of the conduit;

the dispensing port comprising a piezo element which is porous, thereby to permit dispensing from a front side of the element, of fluid contacting the element on a rear side, which is located over the end of the conduit and closes the end of the conduit, and which is drivable to vibrate and thereby dispense fluid from the dispensing port, in use the arrangement being to allow fluid to flow by gravity from the reservoir through the conduit to the piezo element;

a bleed tube communicating at one end with the conduit, between the outlet and the closed end, and extending generally vertically from the conduit to a location above the dispensing port, and including a selectively closeable valve; and a source of below-atmospheric pressure to the portion of the reservoir above the fluid.

2. A dispensing apparatus according to claim 1 in which the source of below-atmospheric pressure comprises a piston.

3. A dispensing apparatus according to claim 2 further comprising an openable cover concealing at least part of the apparatus, wherein the piston is operatively connected to the cover so as to impose below-atmospheric pressure to the reservoir on closing the cover.

4. A dispensing apparatus according to claim 1 further comprising an openable cover concealing at least part of the apparatus, wherein the selectively closeable valve is operatively connected to the cover so as to close the valve on closing the cover.

5. A dispensing apparatus according to claim 1 in which the source of below-atmospheric pressure comprises a piston, further comprising an openable cover concealing at least part of the apparatus, wherein the piston and the selectively closeable valve are operatively connected to the cover so as to impose below-atmospheric pressure to the reservoir and close the valve on closing the cover.

* * * * *

UNITED STATES PATENT AND TRADEMARK OFFICE
CERTIFICATE OF CORRECTION

PATENT NO. : 9,636,431 B2  
APPLICATION NO. : 13/591965  
DATED : May 2, 2017  
INVENTOR(S) : Matthew Teeling and Paul Wonnacott Page 1 of 1

It is certified that error appears in the above-identified patent and that said Letters Patent is hereby corrected as shown below:

Please insert the following foreign application priority data:

-- GB 1115123.0 filed September 1, 2011 --

Signed and Sealed this
Eighth Day of May, 2018

Andrei Iancu
*Director of the United States Patent and Trademark Office*